(12) United States Patent
Warier et al.

(10) Patent No.: US 12,148,158 B2
(45) Date of Patent: Nov. 19, 2024

(54) SYSTEM AND METHOD FOR DETECTING AND QUANTIFYING A PLAQUE/STENOSIS IN A VASCULAR ULTRASOUND SCAN DATA

(71) Applicant: Qure.ai Technologies Private Limited, Maharashtra (IN)

(72) Inventors: Prashant Warier, Maharashtra (IN); Rohan Sahu, Karnataka (IN); Ashish Mittal, Karnataka (IN); Kautuk Trivedi, Karnataka (IN); Preetham Putha, Andhra Pradesh (IN); Manoj Tadepalli, Andhra Pradesh (IN)

(73) Assignee: Qure.ai Technologies Private Limited, Mumbai (IN)

( * ) Notice: Subject to any disclaimer, the term of this patent is extended or adjusted under 35 U.S.C. 154(b) by 0 days.

(21) Appl. No.: 18/371,460

(22) Filed: Sep. 22, 2023

(65) Prior Publication Data

US 2024/0127435 A1 Apr. 18, 2024

(30) Foreign Application Priority Data

Oct. 14, 2022 (IN) .............................. 202221058934

(51) Int. Cl.
  *G06T 7/00* (2017.01)
  *G06T 7/11* (2017.01)
  *G16H 50/20* (2018.01)
(52) U.S. Cl.
  CPC .............. *G06T 7/0012* (2013.01); *G06T 7/11* (2017.01); *G16H 50/20* (2018.01);
  (Continued)

(58) Field of Classification Search
  CPC ..................... G06T 7/0012; G06T 7/11; G06T 2207/10132; G06T 2207/20081;
  (Continued)

(56) References Cited

U.S. PATENT DOCUMENTS 8,229,201 B2 7/2012 Licato
8,313,437 B1 11/2012 Suri
(Continued)

FOREIGN PATENT DOCUMENTS

CN 1765330 B 5/2006
CN 114092744 A 2/2022

*Primary Examiner* — Samah A Beg
*Assistant Examiner* — Winta Gebreslassie

(57) ABSTRACT

The present subject matter discloses a system and method for automatically detecting and quantifying a plaque/stenosis in a vascular ultrasound scan data in real time using Deep learning models. The system receives a video data and selects one or more frames/images for further processing to detect and quantify the plaque in the artery. Based on the selected one or more frames, the system detects a region of interest (ROI) and further processes the ROI. The system selects end points of a deposits of the plaque by taking a maximum length of the plaque in the artery/plaque boundary and determines the orientation of the vascular ultrasound scan. Based on the orientation and the selected end points, the system determines a vessel/artery boundary to identify a size of the plaque. Based on the determined vessel boundary and the orientation, the system determines plaque segments and measures parameters of the plaque.

26 Claims, 3 Drawing Sheets

(52) U.S. Cl.
CPC ............... *G06T 2207/10132* (2013.01); *G06T 2207/20081* (2013.01); *G06T 2207/30101* (2013.01)

(58) Field of Classification Search
CPC . G06T 2207/30101; G06T 2207/10016; G06T 7/90; G06T 2207/30104; G16H 50/20
See application file for complete search history.

(56) References Cited

U.S. PATENT DOCUMENTS

| | | | |
|---|---|---|---|
| 11,324,485 B2 | 5/2022 | Hope et al. | |
| 2011/0257545 A1* | 10/2011 | Suri | A61B 8/5223 |
| | | | 600/508 |
| 2019/0180153 A1* | 6/2019 | Buckler | G06F 18/29 |
| 2023/0394663 A1* | 12/2023 | Min | A61B 5/055 |

* cited by examiner

SYSTEM AND METHOD FOR DETECTING AND QUANTIFYING A PLAQUE/STENOSIS IN A VASCULAR ULTRASOUND SCAN DATA

PRIORITY INFORMATION

The present application does claim priority from Indian Application no. 202221058934 filed on 14 Oct. 2022.

TECHNICAL FIELD

The present subject matter described herein, in general, relates to a medical image processing. Particularly, the invention describes a system and a method for automatically detecting and quantifying a plaque/stenosis in a vascular ultrasound scan data.

BACKGROUND

In general, a medical Ultrasound scan is a diagnostic technique that uses sound waves to capture a continuous stream of images of internal body structures. The continuous stream of images is a set of frames that forms a video (cine loop) that is used to examine internal organs of a patient. Vascular Ultrasound scan is an imaging technique that is used to examine the body's circulatory system to detect blockages in the arteries and veins. Conventionally, during the vascular scanning of a patient, a radiologist/clinician examines the video to detect a presence of a plaque that may be formed as a protrusion on the walls of an artery in the circulatory system. Upon identification of the plaque, an image is captured as a snapshot at a desirable point for measuring and characterizing the plaque. The measurement of the plaque enables the radiologist to determine a length of the plaque and area of plaque coverage within the artery/artery segment. The measurements and characterizing details are disclosed in a final carotid report. Based on the report, the clinician/physician decides a further treatment/strategy to remove the plaque or suppress growth of the plaque, according to a health condition of the patient.

In the conventional procedure, the plaque has to be detected manually by the radiologist during the scanning. Also, the plaque image has to be manually selected from the video for quantification. Here, selection of a best snapshot (image) from the video is critical for accurately measuring (length, area) and characterizing (type, brightness, shape, texture etc.) the plaque. A sub-optimal image selection can lead to errors in diagnosis subsequently. The radiologist has to then perform a tedious process of quantification which involves manual selection of endpoints and boundaries for plaque measurement from the image and a manual detection of probe orientation. Not only is this a time consuming and a tedious task, but one that is error prone and inaccurate. Therefore, there is a need for a system to automatically detect and quantify parameters of the plaque in real-time during the vascular ultrasound scanning.

OBJECTS OF THE INVENTION

Some of the objects of the present disclosure are described herein below:

A main object of the present invention is to provide a system and a method for detecting and quantifying a plaque/stenosis in a vascular ultrasound scan data automatically.

Another object of the present invention is to provide a system and a method for detecting and quantifying a plaque/stenosis in a vascular ultrasound scan data automatically in real time.

Another object of the present invention is to provide a system and a method for detecting and quantifying a plaque/stenosis in a vascular ultrasound scan data automatically using Deep learning models which are fully supervised models.

Another object of the present invention is to provide a system and a method for detecting and quantifying a plaque/stenosis in a vascular ultrasound scan data automatically along a direction of a flow of blood in the artery.

Another object of the present invention is to provide a system and a method for detecting and quantifying a plaque/stenosis in a vascular ultrasound scan data automatically to improve accuracy of plaque/stenosis detection and quantification without much human intervention.

The other objects and advantages of the present invention will be apparent from the following description when read in conjunction with the accompanying drawings, which are incorporated for illustration of preferred embodiments of the present invention and are not intended to limit the scope thereof.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for detecting and quantifying a plaque/stenosis in a vascular ultrasound scan data automatically. This summary is not intended to identify essential features of the claimed subject matter nor is it intended for use in determining or limiting the scope of the claimed subject matter.

According to a first aspect of an embodiment, the present invention provides a system for detecting and quantifying a plaque/stenosis in a vascular ultrasound scan data. The system comprises a memory and at least one processor. The processor comprises a frame quality control module, a frame sampling module and a frame processing module. The frame quality control module is configured to receive a set of frames from a video input of a vascular ultrasound scan data; and select a frame based on quality control parameters of the frame using the Deep Learning models. It should be noted that quality control parameters include noise level and diagnostically acceptable images to measure the plaque length and area of coverage. The frame sampling module is configured to automatically detect a region of interest (ROI) in the selected frame by detecting any protrusions from walls of artery that resembles a plaque using the Deep Learning models. It should be noted that the detected ROI is suspected for the presence of the plaque in the selected frame. It should be noted that the Deep Learning models are trained using a plurality of annotated vascular ultrasound scan data to detect any protrusions from the walls of the artery that resembles the plaque.

The frame processing module is configured to process the selected frame using the Deep Learning models for measuring and characterizing parameters of the plaque that is detected on the vascular ultrasound scan data. The frame processing module further comprises a region detection module, an orientation detection module, a vessel segmentation module, plaque detection module and a plaque measurement module. The region detection module is configured to select end points in the detected ROI of the selected frame of the vascular ultrasound scan data using the Deep learning models. It should be noted that the Deep learning models select the end points in the detected ROI based on a maximum length of the plaque covered in the artery. The orientation detection module is configured to determine an orientation of the detected ROI in the selected frame. The vessel segmentation module is configured to determine vessel boundaries of the detected ROI based on the determined orientation. The plaque detection module is configured to detect plaque segments on the determined vessel boundaries of the detected ROI based on the determined orientation. The plaque measurement module is configured to measure/determine parameters of the plaque from the detected plaque segments and the determined vessel boundaries of the detected ROI using heuristic techniques.

According to the first aspect of the embodiment, the plaque measurement module is configured to measure/determine parameters of the plaque from the detected plaque segments and the determined vessel boundaries of the detected ROI along a direction of a flow of blood in the artery using heuristic techniques. It should be noted that the video input of the vascular ultrasound scan data is a real-time feed or pre-recorded video of the vascular ultrasound scan data. Further, it should be noted that the determined orientation is at least in a longitudinal view or in a transverse view.

According to the first aspect of the embodiment, the longitudinal view indicates the artery as a pipe from one side of the plaque segment and a presence/absence of the plaque on walls of the pipe. It should be noted that when the determined orientation of the detected ROI of the vascular ultrasound scan data is in the longitudinal view, then the parameter measured is a length (L) of the plaque occupied in the artery along the determined vessel boundaries. It should be noted that when the determined orientation of the detected ROI of the vascular ultrasound scan data is in the longitudinal view, then the parameter determined is an area (A) of the protrusions on the walls of an artery along the determined vessel boundaries, based on the measured length of the plaque.

According to the first aspect of the embodiment, the transverse view indicates the artery as a circle and a presence/absence of the plaque within the circle at a circumference of the artery. It should be noted that when the determined orientation is in the transverse view, then the parameter measured is a diameter (D) of the plaque occupied in the artery along the determined vessel boundaries. It should be noted that when the determined orientation is in the transverse view, then the parameter determined is a change in area (AA) of the protrusions on the walls of an artery along the determined vessel boundaries, based on the measured diameter D of the plaque.

According to the first aspect of the embodiment, the frame quality control module is configured to reject an unqualified video frame that is not acceptable for detection of the plaque from the selected frame of the vascular ultrasound scan data, based on a feedback from the frame sampling module and the frame processing module. It should be noted that the Deep Learning model for plaque detection comprise a fully supervised model.

According to a second aspect of an embodiment, the present invention provides a method for detecting and quantifying a plaque/stenosis on vascular ultrasound scan data. The method implemented in a system comprising a memory and at least one processor. The method comprising: receiving, by a processor, a set of frames from a video input of a vascular ultrasound scan data; selecting, by the processor, a frame based on quality control parameters of the frame using the Deep Learning models; it should be noted that the quality control parameters include noise level, diagnostically acceptable frames and the like; detecting, by the processor, a region of interest (ROI) in the selected frame by detecting any protrusions from walls of artery that resembles a plaque using the Deep Learning models. It should be noted that the detected ROI is suspected for the presence of the plaque in the selected frame. It should be noted that the Deep Learning models are trained using a plurality of annotated vascular ultrasound scan data to detect any protrusions from the walls of the artery that resembles the plaque, and processing, by the processor, the selected frame using the Deep Learning models for measuring and characterizing parameters of the plaque that is detected on the vascular ultrasound scan data.

The processing further comprising: selecting end points in the detected ROI of the selected frame of the vascular ultrasound scan data using the Deep learning models. It should be noted that the Deep learning models select the end points in the detected ROI based on a maximum length of the plaque covered in the artery. The processing further comprising determining an orientation of the detected ROI in the selected frame; determining vessel boundaries of the detected ROI based on the determined orientation; detecting plaque segments on the determined vessel boundaries of the detected ROI based on the determined orientation; and measuring/determining parameters of the plaque from the detected plaque segments and the determined vessel boundaries of the detected ROI using heuristic techniques.

According to the second aspect of an embodiment, measuring/determining the parameters of the plaque from the detected plaque segments and the determined vessel boundaries of the detected ROI are performed along a direction of a flow of blood in the artery using heuristic techniques. It should be noted that the video input of the vascular ultrasound scan data is a real-time feed or pre-recorded video of the vascular ultrasound scan data. Further, it should be noted that the determined orientation is at least in a longitudinal view or in a transverse view.

According to the second aspect of the embodiment, the longitudinal view indicates the artery as a pipe from one side of the plaque segment and a presence/absence of the plaque on walls of the pipe. It should be noted that when the determined orientation of the detected ROI of the vascular ultrasound scan data is in the longitudinal view, then the parameter measured is a length (L) of the plaque occupied in the artery along the determined vessel boundaries. It should be noted that when the determined orientation of the detected ROI of the vascular ultrasound scan data is in the longitudinal view, then the parameter determined is an area (A) of the protrusions on the walls of an artery along the determined vessel boundaries, based on the measured length of the plaque.

According to the second aspect of the embodiment, the transverse view indicates the artery as a circle and a presence/absence of the plaque within the circle at a circumference of the artery. It should be noted that when the determined orientation is in the transverse view, then the parameter measured is a diameter (D) of the plaque occupied in the artery along the determined vessel boundaries. It should be noted that when the determined orientation is in the transverse view, then the parameter determined is a change in area (AA) of the protrusions on the walls of an artery along the determined vessel boundaries, based on the measured diameter D of the plaque.

According to the second aspect of the embodiment, the method comprising rejecting, by the processor, an unqualified video frame that is not acceptable for detection of the plaque from the video input of the vascular ultrasound scan data, based on a feedback during sampling and processing. It should be noted that the Deep Learning models for plaque detection comprises a fully supervised model.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures, however, the invention is not limited to the specific apparatus, system and a method for detecting and quantifying a plaque/stenosis in a vascular ultrasound scan data as disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

The embodiments herein and the various features and advantageous details thereof are explained more fully with reference to the non-limiting embodiments and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Some embodiments of this disclosure, illustrating all its features, will now be discussed in detail. The words "determining", "receiving", "processing", "segmenting", "selecting", "characterizing", "detecting", "measuring", "quantifying" and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

Figure 1:
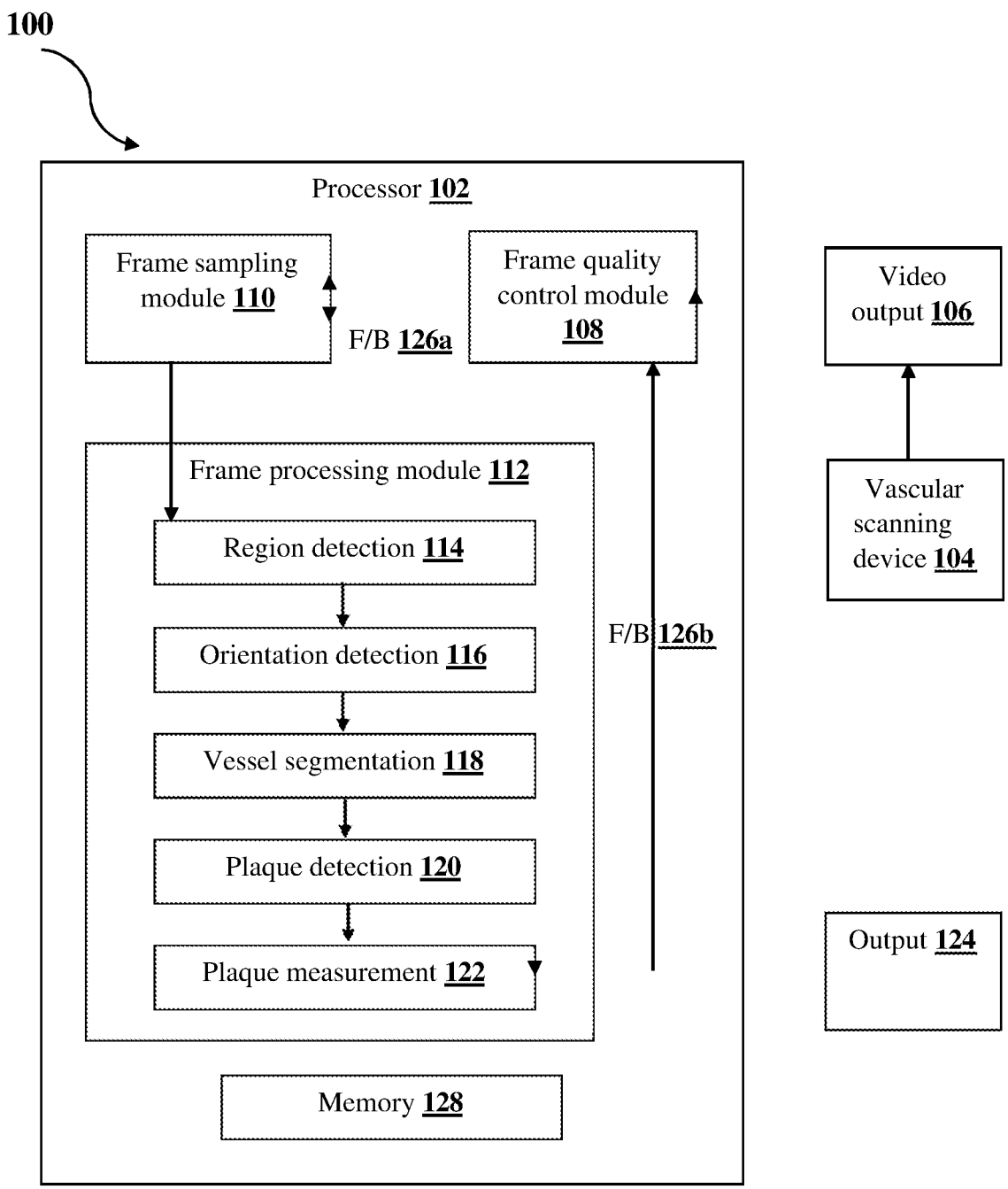
FIG. 1 illustrates a schematic block diagram of a system for detecting and quantifying a plaque/stenosis in a vascular ultrasound scan data, in accordance with a first aspect of an embodiment of the present subject matter.
Figure 2:
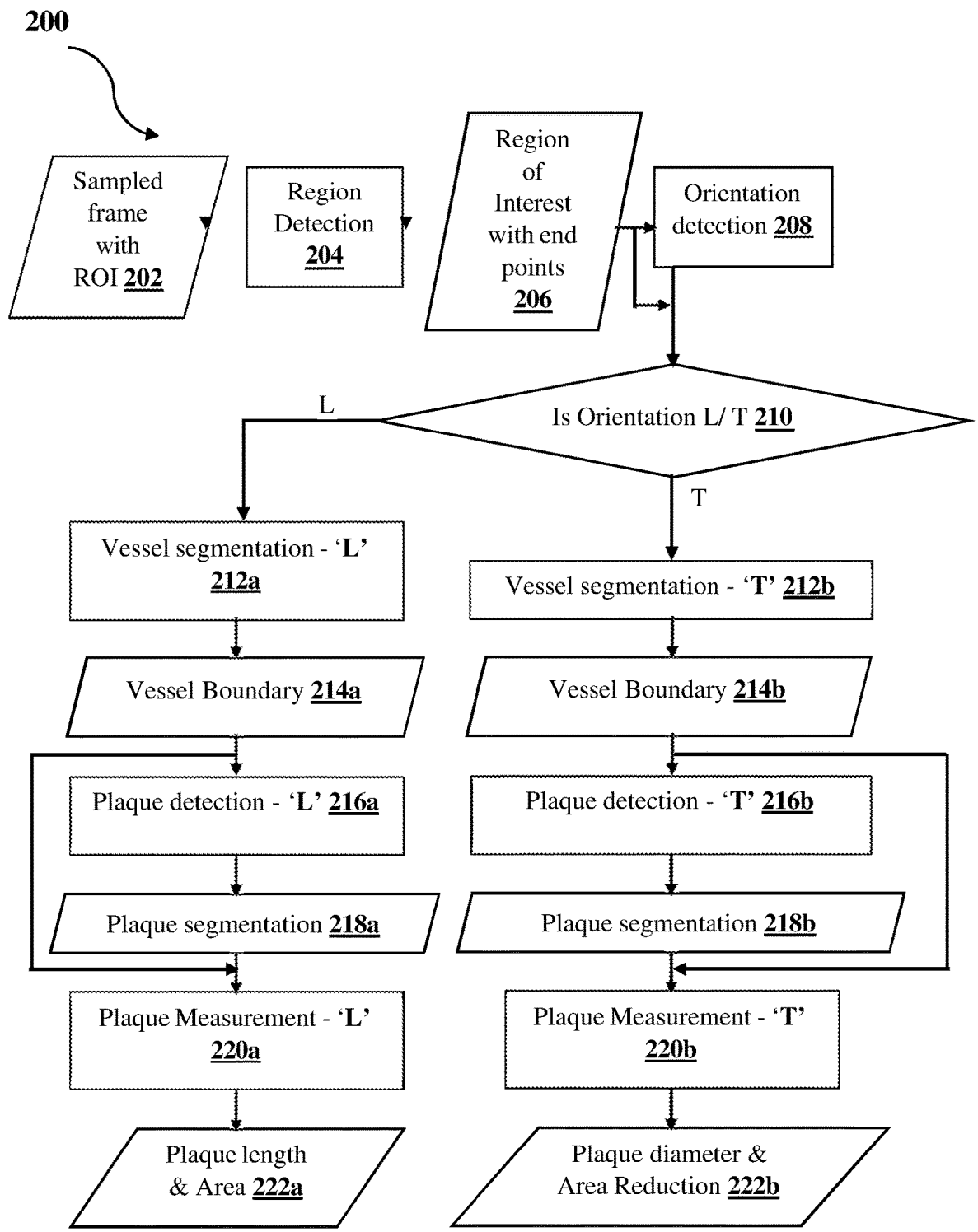
FIG. 2 illustrates a schematic block diagram of a frame processing module for measuring and characterizing parameters of a plaque/stenosis in a vascular ultrasound scan data automatically, in accordance with a first aspect of an embodiment of the present subject matter.
Figure 3:
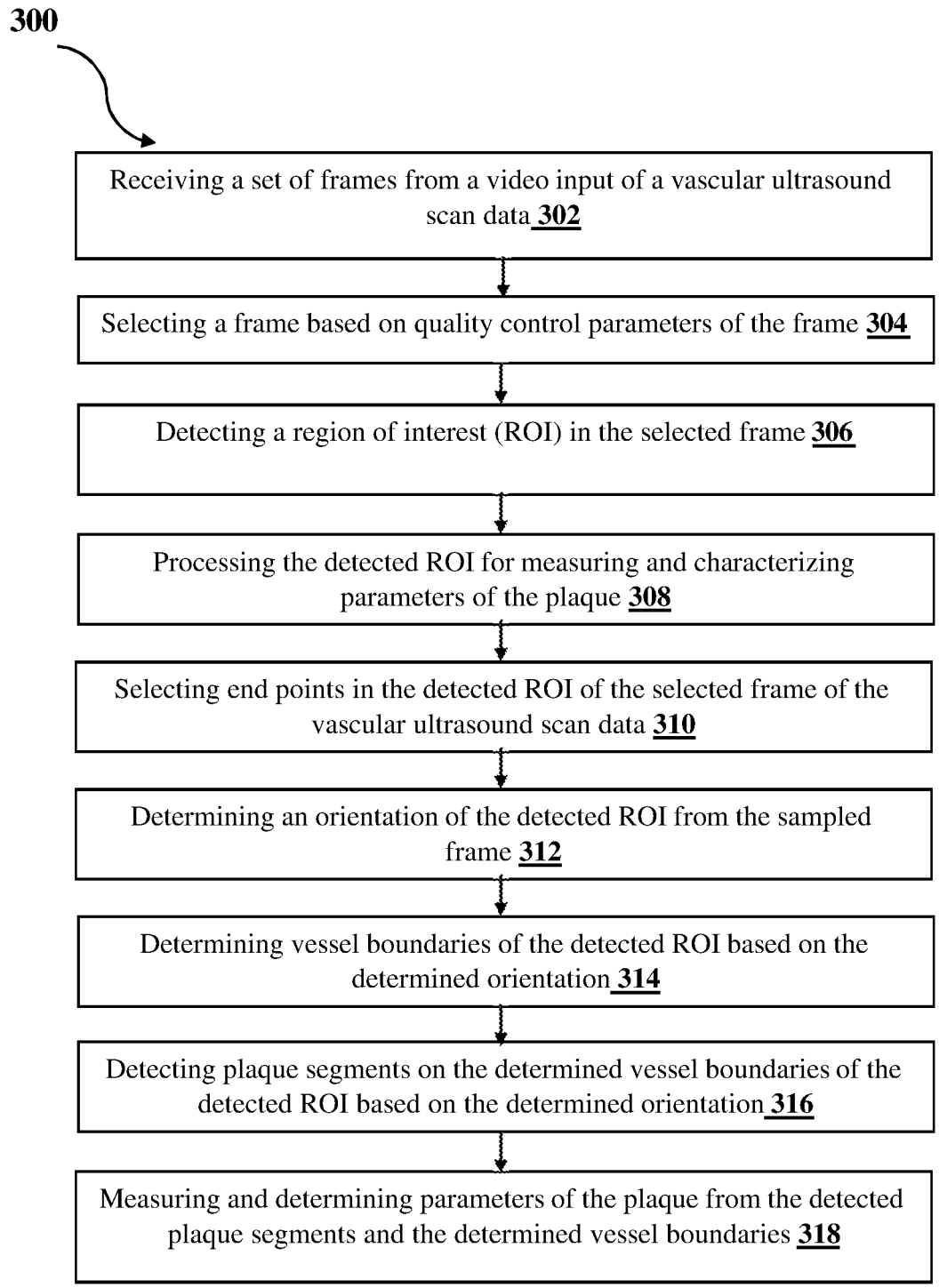
FIG. 3 illustrates a method implemented in a system for detecting and quantifying a plaque/stenosis in a vascular ultrasound scan data automatically, in accordance with a second aspect of an embodiment of the present subject matter.

As mentioned above, the conventional systems can perform the vascular scan imaging/analysis of a patient using pre-stored images. At later time, Radiologist/medical expert can detect the plaque manually using the pre-stored images. In case the pre-stored/captured images are not accurate or clear to measure size of a plaque, then the patient has to schedule an appointment for re-scanning. This may create an additional stress on the patient. Moreover, the Radiologist does not have an option/control over the frame selection along with suggestions from the system. Further, the radiologist has to perform the vascular image analysis with the pre-stored images and this may be lead to inefficient analysis in accuracy point of view. Therefore, there is a need for a system to automatically detect and quantify parameters of the plaque during the vascular ultrasound scanning. The embodiments herein achieve this by providing a system and a method for detecting and quantifying a plaque/stenosis in a vascular ultrasound scan data automatically using Deep Learning Models. The use of deep learning models aids the Radiologist to select good quality frames and detect plaques in real-time and with greater accuracy leading to more efficient diagnosis. In case of multiple plaque detection or more images are required, then the vascular ultrasound scanning can be performed instantaneously. Referring now to the drawings, and more particularly to FIGS. 1 through 3, where similar reference characters denote corresponding features consistently throughout the figures, there are shown preferred embodiments.

The term "quantify" referred herein is measurement of parameters of the plaque or related vessels/artery of a patient. The term "characterizing parameters" referred herein are parameters that can be computed based on observation or measured parameters.

The term "vascular ultrasound scan" referred herein is an image/scan obtained from an ultrasound scanning device for monitoring a flow of blood to organs and tissues throughout a body/anatomy of the human. The term "ultrasound scan data" referred herein is a scan details and/or images regarding the details of the monitored flow of blood to organs and tissues throughout the body/anatomy of the human.

The term "Heuristics" refers to a technique designed for solving a problem more quickly when classic methods are too slow, or for finding an approximate solution when classic methods fail to find any exact solution. This is achieved by trading optimality, completeness, accuracy, or precision for speed. In a way, it can be considered a shortcut. A heuristic function, also called simply a heuristic, is a function that ranks alternatives in search algorithms at each branching step based on available information to decide which branch to follow. The objective of a heuristic is to produce a solution in a reasonable time frame that is good enough for solving the problem at hand. This solution may not be the best of all the solutions to this problem, or it may simply approximate the exact solution.

The present subject matter discloses a system and a method for detecting and quantifying a plaque/stenosis in a vascular ultrasound scan data automatically. The stenosis occurs when the plaque present on the walls of the artery obstructs the flow of blood within an artery. During a vascular ultrasound scanning, the plaque is detected, measured and characterized in B-mode of ultrasound (black & white mode). Whereas, the stenosis is detected and graded in pulse-wave (PW Doppler) mode with color, during the vascular ultrasound scanning.

According to aspects of an embodiment, a system and method for automatically detecting and quantifying a plaque/stenosis in a vascular ultrasound scan data is provided to improve the accuracy of a vascular ultrasound scanning. Particularly, the system provides a solution to perform the vascular ultrasound scanning in real-time. Further, the system utilizes Deep learning models, which are fully supervised to perform the vascular ultrasound scanning in real-time without much human intervention. The system receives video output/data (i.e. set of frames) from a vascular scanning device and selects one or more frames/images that are of a defined quality standard for further processing to detect and quantify the plaque in the artery. Here, the quality of the frame is determined at initial stage using certain parameters (quality control parameters) i.e. proprietary criteria. The parameters are determined by an experienced panel of radiologists & neurologists to acquire frames with a better quality for diagnostic purposes. The parameters may include but are not limited to absence of shadows in the artery, clear visibility of ends of an artery segment or pipe, noise level, intima-medial thickness (IMT), mode of operation such as B-mode, colour mode, Pulsed Wave (PW) Doppler mode, anatomy (i.e. location) of the ultrasound scan (for example, Common carotid artery (CCA), bulb and the like) and so on. For instance, in a B-mode ultrasound scanning, the parameters that have to be mainly considered are: both the ends of the artery (pipe) should be open, IMT should be visible, image without shadows in the artery and the like.

After the system selects one or more frames that meet the defined quality standard, the system detects a region of interest (ROI). It should be noted that the detected ROI is suspected for the presence of the plaque in the selected frame. In other words, the ROI illustrates the presence of the plaque. The system marks the detected ROI and further processes the ROI using Deep learning models which compare the marked ROI with annotated ultrasound scan data of anonymised patient data. Further, the system selects end points of a spread/deposits of the plaque using the Deep Learning models by comparing the detected ROI with a predefined data range of the artery at a particular region of a human anatomy/body.

After selection of the end points, the system determines the orientation of the vascular ultrasound scan. The orientation may be longitudinal view or transverse view. Based on the orientation and the selected end points, the system determines a vessel/artery boundary to identify a size of the plaque. Based on the determined vessel boundary and the orientation, the system determines plaque segments. Using the determined plaque segments and the vessel boundaries, the system determines characteristic features of the plaque. In the longitudinal view, the system measures a length of the plaque and the system determines area of a plaque coverage using image processing techniques. In the transverse view, the system measures a diameter of the plaque and the system determines area of a plaque coverage using image processing techniques. The system updates the training data of the Deep learning models continuously using feedback received from the radiologist through validation. Further, the system updates the training data by a knowledge gained from each vascular scan data with details that are not limited to size of the artery/vessels at different region of a patient at different age groups, presence of plaque or any other misrepresentations such as shadow or artefacts as a plaque and the like. With the knowledge, the training data is updated with additional annotated vascular scan data. For example, the knowledge gained from each vascular scan data is applied to an existing training data so that a new unlabelled training data can get pseudo-labels (for a vessel boundary) without a manual annotation. The pseudo-labels can be used for training a next updated version of a same model. The annotated vascular scan data includes but is not limited to size of the artery, length of the plaque, area of the plaque within a plaque boundary (boundary of the plaque), diameter of the artery, severity level of the plaque/stenosis, plaque area of reduction in the artery, and the like.

Referring now to FIG. 1, a schematic block diagram of a system 100 for detecting and quantifying a plaque/stenosis in a vascular ultrasound scan data is illustrated according to a first aspect of an embodiment. The system 100 for detecting and quantifying a plaque/stenosis in a vascular ultrasound scan data comprises a memory 128 and at least one processor 102. The processor 102 comprises a frame quality control module 108, a frame sampling module 110 and a frame processing module 112. The frame quality control module 112 is configured to receive a set of frames of a video that is output from a vascular ultrasound scanning device 104. It should be noted that the video output 106 from the vascular ultrasound scanning device 104 is a real-time feed of the vascular ultrasound scan. For example, the while performing the vascular ultrasound scan, the video output 106 from an ultrasound scanning device 106 is received by the system 100 which then selects a frame that is suspected for the presence of plaque.

The processing of the video frames in real-time and the detection of plaques using deep learning models during the processing enables the radiologist to instantaneously perform a re-scan in case more images are needed for diagnosis. For example, if a patient is detected with multiple number of plaques/steno sis with similar sizes/dimensions and the Radiologist needs more images to reconfirm a size of the artery and the presence of the plaque, then the Radiologist can perform the diagnosis instantaneously to acquire more details. The advantage of a real-time analysis is that the radiologist may not miss any plaques while scanning and can take the snapshot of a best quality image for the plaque measurement and characterization. Thus, the real-time analysis of the vascular ultrasound scanning avoids the need for calling the patient back again for repetition to get images with the better quality for diagnostic purposes. By this way, time and effort for detecting the plaque can be reduced. Further, the frame quality control module is configured to select a frame based on quality control parameters of the frame using the Deep Learning models. It should be noted that quality control parameters include noise level, diagnostically acceptable frames to measure the plaque length and area of coverage over an artery segment and the like.

The diagnostically acceptable frames are the frames that have an accurate view or a clear view to detect and measure the plaque present in an artery of a vascular system 100. The diagnostically acceptable frames are detected based on the proprietary criteria for training the modules by building consensus with experienced cardiovascular specialists, neurologists, radiologists etc. The frame is selected by capturing a snapshot of the video input with an alert indicated on the video input. The alert may be indicated as an arrow or markings along a flow of the blood through an artery. The snapshot or the captured image is the selected frame for further processing. The frame selection is performed by detecting a change in the walls of the artery using Deep learning models or other image processing techniques. For example, the change in the walls of the artery may be due to a protrusion on the walls of the artery or may be due to an abrupt shrinkage of the artery along the flow of the blood through the artery.

The frame sampling module 110 is configured to detect a region of interest (ROI) in the selected frame by detecting any protrusions from walls of artery that resembles a plaque using the Deep Learning models. It should be noted that the detected ROI is suspected for the presence of the plaque in the selected frame. For example, the frame sampling module 110 may check whether the selected frame contains a ROI or not. The ROI is the presence of plaque in the artery/blood vessel. Alternatively, the ROI can be an abrupt shrinkage of blood vessel (i.e. stenosis). It should be noted that the Deep Learning models are trained using a plurality of annotated vascular ultrasound scan data to detect any protrusions from the walls of the artery that resembles the plaque. The annotated vascular ultrasound scan data is gathered from anonymised ultrasound vascular scan data of patients from different locations. For example, the anonymised ultrasound vascular scan data of the patients from Hospitals, Diagnostic Labs, Medical schools, Incubation centres and so on. Further, the Deep Learning models are continuously trained with Artificial Intelligence (AI) model to identify best frames for detecting the plaque. It should be noted that the selection of the best frames is performed to avoid any lag or error in marking out the plaque. It must be noted that the AI models are able to distinguish plaques from any shadows/artefacts in the video input. Further, it should be noted that the detected ROI is suspected for the presence of the plaque in the selected frame.

The frame processing module 112 is configured to process the selected frame using the Deep Learning models for measuring and characterizing parameters of the plaque that is detected on the vascular ultrasound scan data. The processing of the selected frame includes but is not limited to selection of end points of the detected plaque along the flow of the blood in the artery, determination of ultrasound scan orientation, determination of plaque segmentation, and plaque measurement/quantification. For example, the plaque ultimately obstructs the flow of blood in the artery. Therefore, measuring along directions of flow of the blood in the artery can ensure better accuracy in detecting the plaques' ability to significantly obstruct the flow of the blood. Especially, when the plaque grows in width over time in the artery, the selection of the end points of the detected plaque along the flow of the blood in the artery is accurate. The frame processing module 112 further comprises a region detection module 114, an orientation detection module 116, a vessel segmentation module 118, a plaque detection module 120 and a plaque measurement module 122.

The region detection module 114 is configured to select end points in the detected ROI of the selected frame of the vascular ultrasound scan data using the Deep learning models. It should be noted that the Deep learning models select the end points in the detected ROI based on a maximum length of the plaque covered in the artery. For example, within the detected ROI present on the selected frame/image, a distance or length of the plaque is marked by selecting a starting point and an ending point of the plaque inside the artery. For instance, the end points are selected within the artery by comparing a length and diameter of the artery at that region of a body of the patient with a predefined range of data. That is, the length and diameter of the artery is considered to be within the predefined range for each region of the body of the patient. The Deep learning models decide the end points based on the predefined range of length of the artery and/or based on the training data using anonymized ultrasound image data. For example, the system 100 measures the plaque at points where a plaque detection is most reliable. Then, the Deep learning models enabled with Artificial Intelligence (AI) can recommend when to measure the plaque. This measurement has the benefit over the conventional systems by eventually identifying a maximum length of the plaque. The conventional system may sometimes miss due to a manual measurement.

The orientation detection module 116 is configured to determine an orientation of the detected ROI in the selected frame. Further, it should be noted that the determined orientation is at least in a longitudinal axis/view or in a transverse view/axis. The longitudinal view indicates the artery as a pipe from one side of the plaque segment and a presence/absence of the plaque on walls of the pipe. The transverse view indicates the artery as a circle and a presence/absence of the plaque within the circle at a circumference of the artery.

The vessel segmentation module 118 is configured to determine vessel/artery boundaries of the detected ROI based on the determined orientation. In case of the longitudinal view, the vessel boundaries of the ROI are determined by marking the protrusions on the walls of the artery for the region that is covered within the selected end points. In case of the transverse view, the vessel boundaries of the ROI are determined by marking the protrusions on the circumference of the walls of the artery at each slices/cross-sections of the artery, for the region that is covered within the selected end points. The markings are made by means of colour differentiator for further processing with image processing techniques. Especially, the boundaries illustrate/define a size of the plaque inside the artery.

The plaque detection module 120 is configured to detect plaque segments on the determined vessel boundaries of the detected ROI based on the determined orientation. It should be noted that the plaque segments are determined based on the determined orientation. In case of the longitudinal view, the plaque segments are detected over the length of the vessel boundaries by computing area of coverage at pixel-level segmentation using the markings/masking. In case of the transverse view, the plaque segments are detected for each cross section of the artery for the selected frames. The plaque segments are detected by computing an area of reduction or change in area (marking) at pixel-level segmentation for the region that is covered within the selected end points of the artery.

The plaque measurement module 122 is configured to measure/determine parameters of the plaque from the detected plaque segments and the determined vessel boundaries of the detected ROI using heuristic techniques. The measuring/determining the parameters of the plaque from the detected plaque segments and the determined vessel boundaries of the detected ROI are performed along a direction of a flow of blood in the artery using heuristic techniques. The heuristic techniques include but are not limited to Image processing, contour mapping, pixel-level segmentation and mapping with the artery wall boundary and the like. The measured/determined parameters of the plaque are provided as an output 124 to the radiologist or patient.

According to the first aspect of the embodiment, the plaque measurement module 122 is configured to measure/determine parameters of the plaque from the detected plaque segments and the determined vessel boundaries of the detected ROI along a direction of a flow of blood in the artery using heuristic techniques.

According to the first aspect of the embodiment, the frame quality control module 108 is configured to reject an unqualified video frame that is not acceptable for detection of the plaque from the selected frame of the vascular ultrasound scan data, based on a feedback (F/B) (126a, 126b) from the frame sampling module and the frame processing module. It should be noted that the Deep Learning models for plaque detection comprises a fully supervised models that includes a trained data. The detailed description of the frame processing module based on the determined orientation is described in connection with FIG. 2.

Referring now to FIG. 2, a schematic block diagram 200 of a frame processing module for measuring and characterizing parameters of a plaque/stenosis in a vascular ultrasound scan data automatically based on the determined orientation is illustrated according to the first aspect of an embodiment. The frame processing module is incorporated in a system 100 described in FIG. 1 above for detecting and quantifying the plaque/stenosis in the vascular ultrasound scan data. The frame processing module is configured to process the selected frame using the Deep Learning models for measuring and characterizing parameters of the plaque that is detected on the vascular ultrasound scan data. The frame processing module further comprises a region detection module, an orientation detection module, a vessel segmentation module, plaque detection module and a plaque measurement module. Processes involved in the frame processing module comprises the following steps:

At block 202, at the frame processing module 112 initially, a sampled/selected frame along with a detected region of interest (ROI) is provided to the region detection module for further processing. The sampled frame along with the detected ROI is provided by the frame sampling module. The region of interest illustrates a specific portion of the selected frame (captured frame or snapshot from the video input) which is suspected for the presence of the plaque.

At block 204, after receiving the detected ROI, the region detection module 114 is configured to select end points in the detected ROI of the selected frame of the vascular ultrasound scan data using the Deep learning models. It should be noted that the Deep learning models select the end points in the detected ROI based on a maximum length of the plaque that is covered in the artery. For example, within the detected ROI present on the selected frame/image, a distance or length of the plaque is marked by selecting a starting point and an ending point of the plaque inside the artery. The end points are selected within the artery by comparing a length of the artery at that region of a body of the patient with a predefined range of data. That is, the length of the artery is considered to be fall within the predefined range for each region of the body of the patient. The Deep learning models decides the end points based on the predefined range of length of the artery and/or based on the training data using anonymized ultrasound image data. For example, the system measures the plaque at points where a plaque detection is most reliable. Then, the Deep learning models enabled with Artificial Intelligence (AI) can recommend when to measure the plaque. This measurement has the benefit over the conventional systems by eventually identifying a maximum length of the plaque. The conventional system may sometimes miss due to a manual measurement.

At block 206, the system 100 that comprises the frame processing module 112 provides the determined end points to the orientation detection module 116.

At block 208, after determination of the end points, the orientation detection module 116 is configured to determine an orientation of the detected ROI in the selected frame. It should be noted that the determined orientation is at least in a longitudinal view/axis or in a transverse view/axis. The transverse view indicates the artery as a circle and a presence/absence of the plaque within the circle at a circumference of the artery.

At block 210, the Deep learning model decides whether the view is the longitudinal view or the transverse view. The deep learning model is trained using anonymized vascular ultrasound scan data. It should be noted that the longitudinal view indicates the artery as a pipe from one side of the plaque segment and a presence/absence of the plaque on walls of the pipe. It should be noted that the Deep Learning models are trained using a plurality of annotated vascular ultrasound scan data to detect any protrusions from the walls of the artery that resembles the plaque. The annotated vascular ultrasound scan data is gathered from anonymised ultrasound vascular scan data of patients from different locations. For example, the anonymised ultrasound vascular scan data of the patients from Hospitals, Diagnostic Labs, Medical schools, Incubation centres and so on. Further, the Deep Learning models are continuously trained with Artificial Intelligence (AI) model to identify best frames for detecting the plaque. It should be noted that the selection of the best frames is performed to avoid any lag or error in marking out the plaque. It must be noted that the AI models are able to distinguish plaques from any shadows/artefacts in the video input. Further, it should be noted that the detected ROI is suspected for the presence of the plaque in the selected frame.

At block 212a, the vessel segmentation "L" module is configured to determine vessel boundaries of the detected ROI, in case that the determined orientation is the longitudinal view. In case of the longitudinal view, the vessel boundaries of the ROI are determined by marking the protrusions on the walls of the artery for the region that is covered within the selected end points. The markings are made by means of colour differentiator for further processing with image processing techniques. Especially, the boundaries illustrate/define a size of the plaque inside the artery.

At block 214a, the vessel segmentation "L" module provides the determined vessel boundaries to the plaque detection module, in case that the determined orientation is the longitudinal view.

At block 216a, the plaque detection 'L,' module is configured to detect plaque segments on the determined vessel boundaries of the detected ROI, in case that the determined orientation is longitudinal view. In case of the longitudinal view, the plaque segments are detected over the length of the vessel boundaries by computing area of coverage at pixel-level segmentation using the markings/masking.

At block 218a, the plaque segmentation 'L,' module provides the determined vessel boundaries to the plaque measurement module.

At block 220a, the plaque measurement 'L' module is configured to measure/determine parameters of the plaque from the detected plaque segments and the determined vessel boundaries of the detected ROI using heuristic techniques. The plaque measurement module is configured to measure/determine parameters of the plaque from the detected plaque segments and the determined vessel boundaries of the detected ROI along a direction of a flow of blood in the artery using heuristic techniques.

At block 222a, the plaque measurement 'L' module provides parameters for quantifying the plaque. It should be noted that the parameter measured is a length (L) of the plaque occupied in the artery along the determined vessel boundaries. It should be noted that when the determined orientation of the detected ROI of the vascular ultrasound scan data is in the longitudinal view, then the parameter determined is an area (A) of the protrusions on the walls of an artery along the determined vessel boundaries, based on the measured length of the plaque.

At block 212b, the vessel segmentation "T" module is configured to determine vessel boundaries of the detected ROI, in case that the determined orientation is the transverse view. In case of the transverse view, the vessel boundaries of the ROI are determined by marking the protrusions on the circumference of the walls of the artery at each slices/cross-sections of the artery, for the region that is covered within the selected end points.

At block 214b, the vessel segmentation "T" module provides the determined vessel boundaries to the plaque detection module.

At block 216b, the plaque detection 'T' module is configured to detect plaque segments on the determined vessel boundaries of the detected ROI, in case that the determined orientation is the transverse view. In case of the transverse view, the plaque segments are detected for each cross section of the artery for the selected frames.

At block 218b, the plaque segmentation 'T' module provides the determined vessel boundaries to the plaque measurement module, in case that the determined orientation is the transverse view.

At block 220b, the plaque measurement 'T' module is configured to measure/determine parameters of the plaque from the detected plaque segments and the determined vessel boundaries of the detected ROI using heuristic techniques. The plaque measurement module is configured to measure/determine parameters of the plaque from the detected plaque segments and the determined vessel boundaries of the detected ROI along a direction of a flow of blood in the artery using heuristic techniques.

At block 222b, the plaque measurement 'T' module provides parameters for quantifying the plaque. It should be noted that when the determined orientation is in the transverse view, then the parameter measured is a diameter (D) of the plaque occupied in the artery along the determined vessel boundaries. It should be noted that when the determined orientation is in the transverse view, then the parameter determined is a change in area (ΔA) of the protrusions on the walls of an artery along the determined vessel boundaries, based on the measured diameter D of the plaque.

An exemplary method 300 implemented in a system for detecting and quantifying a plaque/stenosis in a vascular ultrasound scan data automatically is described with reference to FIG. 3. The method 300 is illustrated as a collection of operations in a logical flow graph representing a sequence of operations that can be implemented in hardware, software, firmware, or a combination thereof. The order in which the method steps are described is not intended to be construed as a limitation, and any number of the described method blocks can be combined in any order to implement the methods, or alternate methods. Additionally, individual operations may be deleted from the methods without departing from the scope of the subject matter described herein. In the context of software, the operations represent computer instructions that, when executed by one or more processors, perform the recited operations. Features that are described with reference to FIGS. 1-2 and are not repeated for the sake of brevity.

Referring now to FIG. 3, a method implemented in a system for detecting and quantifying a plaque/stenosis in a vascular ultrasound scan data automatically is illustrated according to a second aspect of the embodiment. The method implemented in a system comprising a memory and at least one processor. According to an embodiment, the method for detecting and quantifying a plaque/stenosis in a vascular ultrasound scan data automatically comprising the steps of:

At block 302, a set of frames from a video that is output from a vascular ultrasound scanning device is received by the processor of the system. It should be noted that the video output of the vascular ultrasound scan data is a real-time feed of the vascular ultrasound scan data. For example, the while performing the vascular ultrasound scan, the video output from an ultrasound scanning device is received by the system which then selects a frame that is suspected for the presence of plaque. The processing of the video frames in real-time and the detection of plaques using deep learning models during the processing enables the radiologist to instantaneously perform a re-scan in case more images are needed for diagnosis. For example, if a patient is detected with multiple number of plaques/stenosis with similar sizes/dimensions and the Radiologist needs more images to reconfirm a size of the artery and the presence of the plaque, then the Radiologist can perform the diagnosis instantaneously to acquire more details. The advantage of a real-time analysis is that the radiologist may not miss any plaques while scanning and can take the snapshot of a best quality image for the plaque measurement and characterization. Thus, the real-time analysis of the vascular ultrasound scanning avoids the need for calling the patient back again for repetition to get images with the better quality for diagnostic purposes. By this way, time and effort for detecting the plaque can be reduced.

At block 304, a frame is selected by the processor of the system based on quality control parameters of the frame using the Deep Learning models. It should be noted that the quality control parameters include noise level, diagnostically acceptable frames to measure the plaque length and area of coverage over an artery segment and the like. The diagnostically acceptable frames are the frames that have an accurate view or a clear view to detect and measure the plaque present in an artery of a vascular system. The diagnostically acceptable frames are detected based on the proprietary criteria for training the modules by building consensus with experienced cardiovascular specialists, neurologists, radiologists etc. The frame is selected by capturing a snapshot of the video input with an alert indicated on the video input. The alert may be indicated as an arrow or markings along a flow of the blood through an artery. The snapshot or the captured image is the selected frame for further processing. The frame selection is performed by detecting a change in the walls of the artery using Deep learning models or other image processing techniques. For example, the change in the walls of the artery may be due to a protrusion on the walls of the artery or may be due to an abrupt shrinkage of the artery along the flow of the blood through the artery.

At block 306, a region of interest (ROI) in the selected frame is detected by detecting any protrusions from walls of the artery that resembles the plaque using the Deep Learning models. It should be noted that the detected ROI is suspected for the presence of the plaque in the selected frame. For example, the system may check whether the selected frame contains a ROI or not. The ROI is the presence of plaque in the artery/blood vessel. Alternatively, the ROI can be an abrupt shrinkage of blood vessel (i.e. stenosis). It should be noted that the Deep Learning models are trained using a plurality of annotated vascular ultrasound scan data to detect any protrusions from the walls of the artery that resembles the plaque. The annotated vascular ultrasound scan data is gathered from anonymised ultrasound vascular scan data of patients from different locations. For example, the anonymised ultrasound vascular scan data of the patients from Hospitals, Diagnostic Labs, Medical schools, incubation centres and so on. Further, the Deep Learning models are continuously trained with Artificial Intelligence (AI) model to identify best frames for detecting the plaque. It should be noted that the selection of the best frames is performed to avoid any lag or error in marking out the plaque. It must be noted that the AI models are able to distinguish plaques from any shadows/artefacts in the video input. Further, it should be noted that the detected ROI is suspected for the presence of the plaque in the selected frame.

At block 308, the selected frame(s) is(are) processed by the processor, using the Deep Learning models for measuring and characterizing parameters of the plaque that is detected on the vascular ultrasound scan data/images. The processing of the selected frame includes but is not limited to selection of end points of the detected plaque along the flow of the blood in the artery, determination of ultrasound scan orientation, determination of plaque segmentation, and plaque measurement/quantification. For example, the plaque ultimately obstructs the flow of blood in the artery. Therefore, measuring along directions of flow of the blood in the artery can ensure better accuracy in detecting the plaques' ability to significantly obstruct the flow of the blood. Especially, when the plaque grows in width over time in the artery, the selection of the end points of the detected plaque along the flow of the blood in the artery is accurate.

At block 310, the processing is further comprising selecting end points in the detected ROI of the selected frame of the vascular ultrasound scan data using the Deep learning models. It should be noted that the Deep learning models select the end points in the detected ROI based on a maximum length of the plaque covered in the artery. For example, within the detected ROI present on the selected frame/image, a distance or length of the plaque is marked by selecting a starting point and an ending point of the plaque inside the artery. For instance, the end points are selected within the artery by comparing a length and diameter of the artery at that region of a body of the patient with a predefined range of data. That is, the length and diameter of the artery is considered to be within the predefined range for each region of the body of the patient. The Deep learning models decide the end points based on the predefined range of length of the artery and/or based on the training data using anonymized ultrasound image data. For example, the system measures the plaque at points where a plaque detection is most reliable. Then, the Deep learning models enabled with Artificial Intelligence (AI) can recommend when to measure the plaque. This measurement has the benefit over the conventional systems by eventually identifying a maximum length of the plaque. The conventional system may sometimes miss due to a manual measurement.

At block 312, the processing further comprising determining an orientation of the detected ROI in the selected frame. Further, it should be noted that the determined orientation is at least in a longitudinal view/axis or in a transverse view/axis. The longitudinal view indicates the artery as a pipe from one side of the plaque segment and a presence/absence of the plaque on walls of the pipe. The transverse view indicates the artery as a circle and a presence/absence of the plaque within the circle at a circumference of the artery.

At block 314, the processing further comprising determining vessel/artery boundaries of the detected ROI based on the determined orientation. In case of the longitudinal view, the vessel boundaries of the ROI are determined by marking the protrusions on the walls of the artery for the region that is covered within the selected end points. In case of the transverse view, the vessel boundaries of the ROI are determined by marking the protrusions on the circumference of the walls of the artery at each slices/cross-sections of the artery, for the region that is covered within the selected end points. The markings are made by means of colour differentiator for further processing with image processing techniques. Especially, the boundaries illustrate/define a size of the plaque inside the artery.

At block 316, the processing further comprising detecting plaque segments on the determined vessel boundaries of the detected ROI based on the determined orientation. It should be noted that the plaque segments are determined based on the determined orientation. In case of the longitudinal view, the plaque segments are detected over the length of the vessel boundaries by computing area of coverage at pixel-level segmentation using the markings. In case of the transverse view, the plaque segments are detected for each cross section of the artery for the selected frames. The plaque segments are detected by computing an area of reduction or change in area (marking) at pixel-level segmentation for the region that is covered within the selected end points of the artery.

At block 318, the processing further comprising measuring/determining parameters of the plaque from the detected plaque segments and the determined vessel boundaries of the detected ROI using heuristic techniques. The measuring/determining the parameters of the plaque from the detected plaque segments and the determined vessel boundaries of the detected ROI are performed along a direction of a flow of blood in the artery using heuristic techniques. The heuristic techniques include but are not limited to Image processing, contour mapping, pixel-level segmentation and mapping with the artery wall boundary and the like.

According to the second aspect of the embodiment, it should be noted that when the determined orientation of the detected ROI of the vascular ultrasound scan data is in the longitudinal view, then the parameter measured is a length (L) of the plaque occupied in the artery along the determined vessel boundaries. It should be noted that when the determined orientation of the detected ROI of the vascular ultrasound scan data is in the longitudinal view, then the parameter determined is an area (A) of the protrusions on the walls of an artery along the determined vessel boundaries, based on the measured length of the plaque.

According to the second aspect of the embodiment, it should be noted that when the determined orientation is in the transverse view, then the parameter measured is a diameter (D) of the plaque occupied in the artery along the determined vessel boundaries. It should be noted that when the determined orientation is in the transverse view, then the parameter determined is a change in area ($\Delta A$) of the protrusions on the walls of an artery along the determined vessel boundaries, based on the measured diameter D of the plaque.

According to the second aspect of the embodiment, the method further comprising rejecting an unqualified video frame that is not acceptable for detection of the plaque from the video input of the vascular ultrasound scan data, based on a feedback during sampling/frame selecting and processing. The unqualified video frames are the frames that cannot illustrate the plaque segment clearly; or the frames that does not show the plaque; or orientation (longitudinal or transverse view) required for the plaque is not appropriate for detection and so on. It should be noted that the Deep Learning models for plaque detection comprises a fully supervised models that includes a trained data.

According to a third aspect of an embodiment, the present invention provides a computer-readable storage medium, on which a computer program is stored, which when executed by a processor, implements the steps described above in FIG. 3 for detecting and quantifying a plaque/stenosis in a vascular ultrasound scan data automatically. The computer-readable storage medium includes but is not limited to a magnetic disk, an optical disk, a magneto-optical disk, a semiconductor memory, and the like.

Exemplary embodiments discussed above may provide certain advantages. Though not required to practice aspects of the disclosure, these advantages may include those provided by the following features.

Some embodiments of the system and method for detecting and quantifying a plaque/stenosis in a vascular ultrasound scan data automatically improves the measurement and characterization of the plaque/stenosis present in the artery of a vascular ultrasound scan.

Some embodiments of the system and method for detecting and quantifying a plaque/stenosis in a vascular ultrasound scan data automatically can improve accuracy of measurement of the plaque.

Some embodiments of the system and method for detecting and quantifying a plaque/stenosis in a vascular ultrasound scan data automatically using the Deep learning models can also avoid a human intervention. The Deep learning models are fully supervised models, which continuously learn from a feedback of a user during processes involved in the frame processing module and frame sampling module.

Some embodiments of the system and method for detecting and quantifying a plaque/stenosis in a vascular ultrasound scan data automatically can reduce the risk of false identification of the plaque and/or misrepresentation of the plaque.

Some embodiments of the system and method for detecting and quantifying a plaque/stenosis in a vascular ultrasound scan data automatically can detect more plaques and measure them more accurately due to continuous tracking of the plaque to identify the image with longest length or max area.

Some embodiments of the system and method for detecting and quantifying a plaque/stenosis in a vascular ultrasound scan data automatically can remove subjectivity in plaque detection and measurement leading to standardisation of scans, reduction in inter-observer variability and more accurate vascular reporting.

Some embodiments of the system and method for detecting and quantifying a plaque/stenosis in a vascular ultrasound scan data automatically can be used by clinicians (who are not specially trained for vascular imaging) without a skill set in medical imaging can accurately detect and measure plaques in the artery.

Although implementations for detecting and quantifying a plaque/stenosis in a vascular ultrasound scan data automatically have been described in language specific to structural features, it is to be understood that the appended claims are not necessarily limited to the specific features or methods described. Rather, the specific features are disclosed as examples of implementations for detecting and quantifying a plaque/stenosis in a vascular ultrasound scan data automatically.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A system for detecting and quantifying a plaque/stenosis in a vascular ultrasound scan data, wherein the system comprises:
 a memory and at least one processor, wherein the processor comprises:
  a frame quality control module configured to:
   receive a set of frames from a video output of a vascular ultrasound scanning device; and
   select a frame based on quality control parameters of the frame using a Deep Learning model;
   a frame sampling module configured to detect a region of interest (ROI) in the selected frame by detecting any protrusions from walls of artery that resembles a plaque using the Deep Learning model, wherein the Deep Learning model is trained using a plurality of annotated vascular ultrasound scan data, wherein the deep learning model is configured to compare the detected ROI with a predefined data range of wall of the artery; and
   a frame processing module configured to process the detected ROI using the Deep Learning model for measuring and characterizing parameters of the plaque that is detected on the vascular ultrasound scan data, wherein the frame processing module comprises:
a region detection module configured to select end points in the detected ROI of the selected frame of the vascular ultrasound scan data using the Deep learning models; wherein the Deep learning models select the end points in the detected ROI based on a maximum length of the plaque covered in the artery;
an orientation detection module configured to determine an orientation of the detected ROI in the selected frame;
a vessel segmentation module configured to determine vessel boundaries of the detected ROI based on the determined orientation;
a plaque detection module configured to detect plaque segments on the determined vessel boundaries of the detected ROI based on the determined orientation; and
a plaque measurement module configured to measure/determine parameters of the plaque from the detected plaque segments and the determined vessel boundaries of the detected ROI using heuristic techniques.

2. The system as claimed in claim 1, wherein the plaque measurement module is configured to measure/determine parameters of the plaque from the detected plaque segments and the determined vessel boundaries of the detected ROI along a direction of a flow of blood in the artery using heuristic techniques.

3. The system as claimed in claim 1, wherein the video input of the vascular ultrasound scan data is a real-time feed.

4. The system as claimed in claim 1, wherein the determined orientation is at least in a longitudinal view or in a transverse view.

5. The system as claimed in claim 4, wherein the longitudinal view indicates the artery as a pipe from one side of the plaque segment and a presence/absence of the plaque on walls of the pipe.

6. The system as claimed in claim 4, wherein when the determined orientation of the detected ROI of the vascular ultrasound scan data is in the longitudinal view, then the parameter measured is a length (L) of the plaque occupied in the artery along the determined vessel boundaries.

7. The system as claimed in claim 4, wherein when the determined orientation of the detected ROI of the vascular ultrasound scan data is in the longitudinal view, then the parameter determined is an area (A) of the protrusions on the walls of an artery along the determined vessel boundaries, based on the measured length of the plaque.

8. The system as claimed in claim 4, wherein the transverse view indicates the artery as a circle and a presence/absence of the plaque within the circle at a circumference of the artery.

9. The system as claimed in claim 4, wherein when the determined orientation is in the transverse view, then the parameter measured is a diameter (D) of the plaque occupied in the artery along the determined vessel boundaries.

10. The system as claimed in claim 4, wherein when the determined orientation is in the transverse view, then the parameter determined is a change in area ($\Delta A$) of the protrusions on the walls of an artery along the determined vessel boundaries, based on the measured diameter D of the plaque.

11. The system as claimed in claim 1, wherein the frame quality control module is configured to reject an unqualified video frame that is not acceptable for detection of the plaque from the selected frame of the vascular ultrasound scan data, based on a feedback from the frame sampling module and the frame processing module.

12. The system as claimed in claim 1, wherein the Deep Learning models for plaque detection comprises a fully supervised models that includes a trained data.

13. The system as claimed in claim 1, wherein the quality control parameters include noise level, absence of shadows in the artery, visibility of IMT, open ends of the pipe on both sides of the artery, diagnostically acceptable frames and the like.

14. A method for detecting and quantifying a plaque/stenosis in a vascular ultrasound scan data, wherein the method implemented in a system comprising a memory and at least one processor, the method comprising:
receiving, by a processor, a set of frames from a video output of a vascular ultrasound scanning device;
selecting, by the processor, a frame based on quality control parameters of the frame using a Deep Learning model;
detecting, by the processor, a region of interest (ROI) in the selected frame by detecting any protrusions from walls of artery that resembles a plaque using the Deep Learning model, wherein the Deep Learning models are trained using a plurality of annotated vascular ultrasound scan data, wherein the deep learning model is configured to compare the detected ROI with a predefined data range of wall of the artery; and
processing, by the processor, the detected ROI using the Deep Learning models for measuring and characterizing parameters of the plaque that is detected on the vascular ultrasound scan data;
wherein the processing comprising:
selecting end points in the detected ROI of the selected frame of the vascular ultrasound scan data using the Deep learning models; wherein the Deep learning models select the end points in the detected ROI based on a maximum length of the plaque covered in the artery;
determining an orientation of the detected ROI in the selected frame;
determining vessel boundaries of the detected ROI based on the determined orientation;
detecting plaque segments on the determined vessel boundaries of the detected ROI based on the determined orientation; and
measuring/determining parameters of the plaque from the detected plaque segments and the determined vessel boundaries of the detected ROI using heuristic techniques.

15. The method as claimed in claim 14, wherein measuring/determining the parameters of the plaque from the detected plaque segments and the determined vessel boundaries of the detected ROI is performed along a direction of a flow of blood in the artery using heuristic techniques.

16. The method as claimed in claim 14, wherein the video input of the vascular ultrasound scan data is a real-time feed of the vascular ultrasound scan data.

17. The method as claimed in claim 14, wherein the determined orientation is at least in a longitudinal view or in a transverse view.

18. The method as claimed in claim 17, wherein the longitudinal view indicates the artery as a pipe from one side of the plaque segment and a presence/absence of the plaque on walls of the pipe.

19. The method as claimed in claim 17, wherein the transverse view indicates the artery as a circle and a presence/absence of the plaque within the circle at a circumference of the artery.

20. The method as claimed in claim 17, wherein when the determined orientation of the detected ROI of the vascular ultrasound scan data is in the longitudinal view, then the parameter measured is a length (L) of the plaque occupied in the artery along the determined vessel boundaries.

21. The method as claimed in claim 17, wherein when the determined orientation of the detected ROI of the vascular ultrasound scan data is in the longitudinal view, then the parameter determined is an area (A) of the protrusions on the walls of an artery along the determined vessel boundaries, based on the measured length of the plaque.

22. The method as claimed in claim 17, wherein when the determined orientation is in the transverse view, then the parameter measured is a diameter (D) of the plaque occupied in the artery along the determined vessel boundaries.

23. The method as claimed in claim 17, wherein when the determined orientation is in the transverse view, then the parameter determined is a change in area ($\Delta A$) of the protrusions on the walls of an artery along the determined vessel boundaries, based on the measured diameter D of the plaque.

24. The method as claimed in claim 14, wherein the method comprising rejecting, by the processor, an unqualified video frame that is not acceptable for detection of the plaque from the video input of the vascular ultrasound scan data, based on a feedback during sampling and processing.

25. The method as claimed in claim 14, wherein the Deep Learning models for plaque detection comprises a fully supervised models that includes a training data.

26. The method as claimed in claim 14, wherein the quality control parameters include noise level, absence of shadows in the artery, visibility of IMT, open ends of the pipe on both sides of the artery, diagnostically acceptable frames and the like.

* * * * *